United States Patent [19]

Inaba et al.

[11] Patent Number: 5,481,053
[45] Date of Patent: Jan. 2, 1996

[54] PROCESS FOR PREPARING ALPH-METHYLSTYRENE UNSATURATED DIMER

[75] Inventors: Masashi Inaba; Shiroh Inui; Hideki Kurokawa; Fujio Mizutani, all of Mie, Japan

[73] Assignee: Mitsubishi Chemical Corporation, Tokyo, Japan

[21] Appl. No.: 310,395

[22] Filed: Sep. 22, 1994

[30] Foreign Application Priority Data

Sep. 22, 1993 [JP] Japan .................................. 5-257502
Dec. 7, 1993 [JP] Japan .................................. 5-339829

[51] Int. Cl.$^6$ ............................ C07C 2/72; C07C 2/74
[52] U.S. Cl. ...................... 585/406; 585/428; 585/429; 585/435
[58] Field of Search ................................ 585/406, 428, 585/429, 435

[56] References Cited

U.S. PATENT DOCUMENTS 4,199,481   4/1980   Hall et al. ............................... 585/406
4,329,529   5/1982   Nambu ..................................... 585/20

*Primary Examiner*—Asok Pal
*Assistant Examiner*—E. D. Irzinski
*Attorney, Agent, or Firm*—Oblon, Spivak, McClelland, Maier & Neustadt

[57] ABSTRACT

A process for preparing unsaturated dimers of α-methylstyrene comprising dimerizing α-methylstyrene using activated clay or acid clay as a catalyst, in which the dimerization is carried out in the presence of a carbonic acid ester, preferably ethylene carbonate, which process achieves high selectivity to unsaturated dimers with ease in controlling the reaction temperature.

6 Claims, No Drawings

PROCESS FOR PREPARING ALPH-METHYLSTYRENE UNSATURATED DIMER

FIELD OF THE INVENTION

This invention relates to a process for preparing unsaturated dimers of α-methylstyrene. More particularly, it relates to a process for preparing unsaturated dimers of α-methylstyrene comprising dimerizing α-methylstyrene using activated clay or acid clay as a catalyst.

An unsaturated dimer of α-methylstyrene is useful as a raw material of a lubricant for traction drive, a solvent for coatings, and a chain transfer reagent for polymerization reaction.

BACKGROUND OF THE INVENTION

It is known that dimerization of α-methylstyrene under an acidic condition gives 1,1,3-trimethyl-3-phenylindane as a saturated dimer, 2,4-diphenyl-4-methyl-1-pentene and 2,4-diphenyl-4-methyl-2-pentene as unsaturated dimers, and 2,4,6-triphenyl-4,6-dimethyl-1-heptene, etc. as trimers.

Of these oligomers, the unsaturated dimers are useful for their applicability. Known processes for selectively obtaining the unsaturated dimers include dimerization of α-methylstyrene in the presence of a solid acid, such as activated clay or acid clay, or a cation exchange resin as a catalyst and an approximately equivalent amount of water or a polyhydric alcohol (cf. JP-A-48-44240, the term "JP-A" as used herein means an "unexamined published Japanese patent application"). However, when activated clay or acid clay is mixed with water or a polyhydric alcohol, the catalyst undergoes aggregation due to its high affinity for water or the polyhydric alcohol and fails to function effectively, resulting in a low reaction rate. Additionally, the catalyst tends to aggregate and makes fouling on the wall of the reactor.

A dimerization process for α-methylstyrene using a solid acid catalyst with a polyethylene glycol monoalkyl ether as a co-catalyst has been proposed (cf. JP-A-63-192727). In this process, a polyethylene glycol monoalkyl ether is used in an amount of from 0.001 to 0.06% by weight based on the starting material. The process has a disadvantage in that the reaction temperature control is practically difficult because of reaction heat.

SUMMARY OF THE INVENTION

An object of the present invention is to provide a process for dimerizing α-methylstyrene at high selectivity to unsaturated dimers with ease in controlling the reaction temperature.

The present invention provides a process for preparing unsaturated dimers of α-methylstyrene comprising dimerizing α-methylstyrene using activated clay or acid clay as a catalyst, in which the dimerization is carried out in the presence of a carbonic acid ester as a reaction controlling reagent.

The process of the present invention achieves high production selectivity to the useful unsaturated dimers and affords facility in temperature control.

In a preferred embodiment of the present invention, ethylene carbonate is used as a reaction controlling reagent. According to this embodiment, the reaction controlling reagent can easily be separated from the reaction product through phase separation, making it easy to purify the desired unsaturated dimers. The recovered catalyst and especially reaction controlling reagent can be recycled as such for the dimerization reaction without purification.

DETAILED DESCRIPTION OF THE INVENTION

The activated clay or acid clay which can be used as a catalyst is not particularly limited, and any of commercially available ones can be used as such.

While not limiting, the activated clay or acid clay is usually used in an amount of from 0.0005 to 0.1 part by weight, preferably from 0.002 to 0.05 part by weight, per part by weight of α-methylstyrene. The larger the amount of the catalyst, the lower the selectivity to unsaturated dimers. The smaller the amount of the catalyst, the lower the reaction rate of the starting material.

The carbonic acid ester which can be added to the reaction system is not particularly limited. Illustrative examples of suitable carbonic acid esters include acyclic aliphatic carbonic acid esters having 3 to 20 carbon atoms, such as dimethyl carbonate and diethyl carbonate; cyclic aliphatic carbonic acid esters having 3 to 20 carbon atoms, such as ethylene carbonate and propylene carbonate; and aromatic carbonic acid esters having 13 to 30 carbon atoms, such as diphenyl carbonate, with ethylene carbonate being preferred. In using ethylene carbonate, in particular, separation of the reaction product is easy.

The carbonic acid ester is used in an amount of from 0.05 to 1 part by weight, preferably from 0.1 to 0.5 part by weight, per part by weight of α-methylstyrene. If the amount of the carbonic acid ester is less than 0.05 part, the effect of diluting the starting material is insubstantial, making temperature control difficult. If it exceeds 1 part, the production efficiency tends to be reduced.

The amount of carbonic acid ester, from 0.05 to 1 part by weight, per part by weight of α-methylstyrene, enables α-methylstylene to be added dropwise and makes it easy to control the reaction temperature. On the other hand, in the case of the process using polyalkylene glycol monoalkyl ether as co-catalyst mentioned above, the amount of polyalkylene glycol monoalkyl ether is too small to add α-methylstyrene dropwise. Moreover, when increased amount of this co-catalyst is used, the catalyst activity becomes drastically low. If an inert solvent is used for making reaction temperature control easy, the reaction and purification system would become complicated.

The reaction temperature ranges usually from 50° to 150° C., preferably from 70° to 130° C. If it is lower than 50° C., the reaction rate is low, impractically extending the reaction time. If it exceeds 150° C., the selectivity to unsaturated dimers would be reduced and temperature control tends to become difficult.

The reaction time is usually from 1 to 10 hours, preferably from 2 to 5 hours. A shorter reaction time only results in a low conversion of the starting material, and a longer reaction time leads to a reduction in selectivity to unsaturated dimers.

While the reaction pressure is not particularly limited, the reaction is usually conducted under atmospheric pressure.

The reaction may be effected either in a batch system or in a continuous system. Since activated clay or acid clay is generally available as fine particles, a batch system is suitable. In carrying out the reaction in a batch system, a catalyst and a carbonic acid ester are mixed together, and the starting material is added thereto either all at once or in divided portions, with the latter mode of addition being preferred for temperature control.

While the reaction may be performed in an inert solvent, such as $C_{5-20}$ saturated aliphatic or alicyclic hydrocarbons, solvent is not essential because of ease of temperature control.

After completion of the reaction, the reaction mixture can be worked up in an arbitrary manner. The reaction mixture is usually filtered to remove the catalyst, and the filtrate is subjected to distillation to obtain desired unsaturated dimers.

The above-mentioned preferred embodiment will be explained in detail. When ethylene carbonate is used as a reaction controlling reagent, the reaction mixture undergoes phase separation into a phase mainly comprising the unreacted starting material and the reaction product and a phase mainly comprising the catalyst and ethylene carbonate. The desired reaction product, i.e., α-methylstyrene unsaturated dimers, can be recovered from the former phase, while the catalyst and ethylene carbonate can be recovered from the latter phase and recycled as such for the same reaction without purification.

The reaction is usually carried out at 50° to 150° C., preferably 70° to 140° C., still preferably 85° to 130° C.

The reaction mixture is usually obtained as a liquid containing the catalyst used, which undergoes phase separation at 85° C. or lower.

The upper layer mainly comprises the unreacted starting material, a saturated dimer, unsaturated dimers, and high-boiling substances including trimers and higher oligomers of α-methylstyrene, while the lower liquid layer or solid phase mainly comprises ethylene carbonate and the catalyst. After completion of the reaction, the phase separation is carried out as follows.

Liquid-liquid separation is carried out at a temperature range 35° to 85° C., preferably between 40° and 80° C. Liquid-liquid separation can be carried out by, for example, (1) at first removing the catalyst from the reaction mixture by filtration, and allowing the filtrate to settle to cause phase separation, followed by liquid-liquid separation, or (2) without removing the catalyst by filtration, allowing the reaction mixture to stand to separate two liquid phases and removing ethylene carbonate together with the catalyst. On the other hands, solid-liquid separation is effected at a temperature lower than 35° C., preferably between −20° and 30° C. Solid-liquid separation can be carried out by, for example, (1) at first separating the catalyst from the reaction mixture by filtration above 35° C., and cooling the filtrate to precipitate ethylene carbonate, followed by solid-liquid separation to obtain precipitated ethylene carbonate, or (2) without removing the catalyst, cooling the reaction mixture, and separating precipitated ethylene carbonate and the catalyst as a solid mixture. The separated phase mainly comprising ethylene carbonate with or without the catalyst can be recycled for the dimerization reaction without purification.

At temperatures higher than 85° C., phase separation does not occur, and the reaction mixture cannot be separated in phases. Solid-liquid separation when effected at temperatures lower than −20° C. affords no advantage.

While not limiting, the phase mainly comprising the unsaturated dimers of α-methylstyrene obtained by phase separation is generally purified by distillation. Distillation may be under atmospheric pressure or reduced pressure, but reduced pressure is preferred for fear of reduction in recovery due to thermal deterioration of the product. Distillation may be carried out either in a batch system or in a continuous system. The unreacted starting material recovered by the purification step can be recycled for the dimerization reaction.

The present invention will now be illustrated in greater detail by way of Examples, but it should be understood that the present invention is not construed as being limited thereto.

EXAMPLE 1

In a reactor equipped with a reflux condenser, a stirrer, and a thermometer were charged 1 g of activated clay Silton-S (produced by Mizusawa Kagaku K. K.) and 50 g of ethylene carbonate, and the mixture was heated up to 120° C. on an oil bath with stirring. To the mixture was added dropwise 150 g of α-methylstyrene over a period of 40 minutes and the reaction mixture was allowed to react for 4 hours while maintaining the oil bath temperature constant. During the course of reaction, the temperature of the reaction mixture did not exceed the oil bath temperature.

After completion of the reaction, the reaction product was analyzed by gas chromatography to obtain a conversion of α-methylstyrene and selectivities to a saturated dimer (1,1,3-trimethyl-3-phenylindane (hereinafter abbreviated as indane)), unsaturated dimers (2,4-diphenyl-4-methyl-1-pentene (hereinafter abbreviated as 1-pentene) and 2,4-diphenyl-4-methyl-2-pentene (hereinafter abbreviated as 2-pentene)), and trimers and higher oligomers (hereinafter inclusively referred to as high-boiling substances). The results obtained are shown in Table 1 below.

EXAMPLES 2 AND 3

The same procedure as in Example 1 was repeated, except for replacing ethylene carbonate with each of the carbonic acid esters shown in Table 1. The results are shown in Table 1.

In any of the foregoing Examples, no aggregation of the catalyst in the reaction mixture was observed.

COMPARATIVE EXAMPLE 1

The same procedure as in Example 1 was repeated, except that 7 g of ethylene glycol was used in place of ethylene carbonate, α-methylstyrene was added all at once, and the addition of α-methylstyrene was followed by heating to 135° C. at which the reaction was conducted. Continuous observation of the reaction mixture from the start of the reaction revealed blocking of the catalyst. The conversion of α-methylstyrene was 8.9%. The results obtained are shown in Table 1.

COMPARATIVE EXAMPLE 2

The same procedure as in Example 1 was repeated, except for replacing ethylene carbonate with diethylene glycol monoethyl ether. The conversion of α-methylstylene was 26.5%. The results obtained are shown in Table 1.

COMPARATIVE EXAMPLE 3

The same procedure as in Comparative Example 2 was repeated, except for changing the amount of diethylene glycol monoethyl ether to 5 g and adding α-methylstyrene all at once before heating. In the course of elevating the temperature of the reaction mixture, the temperature of the reaction mixture exceeded the oil bath temperature due to the heat of reaction. The temperature control was so difficult that the heating was suspended, and the reaction was resumed at a prescribed temperature. The reaction results are shown in Table 1.

TABLE 1

| Example No. | Amount of Catalyst (g) | Additive Kind | Additive Amount (g) | Reaction Temp. (°C.) | Reaction Time (hr) | Conversion of α-methylstyrene (%) | Selectivity (%) Indane | 1-Pentene | 2-Pentene | High-Boiling Substances |
| --- | --- | --- | --- | --- | --- | --- | --- | --- | --- | --- |
| Example 1 | 1.0 | ethylene carbonate | 50.0 | 120 | 4 | 92.5 | 2.7 | 84.7 | 9.1 | 3.5 |
| Example 2 | 1.0 | propylene carbonate | 50.0 | 120 | 4 | 90.0 | 5.7 | 80.6 | 7.6 | 6.1 |
| Example 3 | 1.0 | diethyl carbonate | 50.0 | 120 | 4 | 93.3 | 6.1 | 76.5 | 13.6 | 3.8 |
| Compara. Example 1 | 1.0 | ethylene glycol | 7.0 | 135 | 4 | 8.9 | 1.8 | 92.4 | 4.3 | 1.5 |
| Compara. Example 2 | 1.0 | diethylene glycol monoethyl ether | 50.0 | 120 | 4 | 26.5 | 0.2 | 95.8 | 3.2 | 0.8 |
| Compara. Example 3 | 1.0 | diethylene glycol monoethyl ether | 5.0 | 120 | 4 | 87.7 | 0.5 | 91.7 | 4.6 | 3.2 |

EXAMPLE 4

In a reactor equipped with a reflux condenser, a stirrer, and a thermometer were charged 4 g of activated clay Silton-S and 200 g of ethylene carbonate, and the mixture was heated up to 120° C. on an oil bath with stirring. To the mixture was added dropwise 600 g of α-methylstyrene over a period of 40 minutes and the reaction mixture was allowed to react for 4 hours while maintaining the oil bath temperature constant. During the reaction, the temperature of the reaction mixture did not exceed the oil bath temperature.

After completion of the reaction, the reaction mixture was cooled to 70° C., followed by filtration to separate the catalyst. The filtrate was allowed to settle at 50° C. whereupon it separated into two layers to obtain 625 g of the upper layer and 170 g of the lower layer. The upper layer was found to comprise 7.4% by weight of the unreacted α-methylstyrene, 2.5% by weight of a saturated dimer, 86.8% by weight of unsaturated dimers, and 3.3% by weight of trimers. The upper layer was distilled under reduced pressure (1333 Pa) to recover 410 g of the unsaturated dimers.

EXAMPLE 5

The same procedure as in Example 4 was repeated, except for replacing 200 g of ethylene carbonate with a mixture of 170 g of the lower layer mainly comprising ethylene carbonate which was obtained by phase separation in Example 4 and 30 g of fresh ethylene carbonate. There was obtained 414 g of unsaturated dimers.

EXAMPLE 6

α-Methylstyrene was dimerized in the same manner as in Example 4. The resulting reaction mixture was filtered to separate the catalyst, and the filtrate was cooled to 15° C. to precipitate ethylene carbonate. After solid-liquid separation, the recovered liquid phase was subjected to distillation to obtain 405 g of unsaturated dimers.

EXAMPLE 7

α-Methylstyrene was dimerized in the same manner as in Example 4, except for replacing 200 g of ethylene carbonate with a mixture of 190 g of the solid phase mainly comprising ethylene carbonate which was obtained in Example 6 and 10 g of fresh ethylene carbonate. After completion of the reaction, the reaction mixture was cooled to 15° C. to solidify the ethylene carbonate, and the liquid phase was recovered therefrom by solid-liquid separation and distilled to obtain 412 g of unsaturated dimers.

EXAMPLE 8

The same procedure as in Example 7 was repeated, except for replacing the mixture of the solid phase obtained in Example 6 and fresh ethylene carbonate with a mixture of 190 g of the solid phase mainly comprising activated clay Silton-S and ethylene carbonate which was obtained in Example 7 with 10 g of fresh ethylene carbonate and adding no fresh catalyst. The liquid phase was recovered in the same manner as in Example 7 and distilled to obtain 402 g of unsaturated dimers.

REFERENCE EXAMPLE 1

α-Methylstyrene was dimerized in the same manner as in Example 4, except for replacing ethylene carbonate with propylene carbonate. The catalyst was removed from the reaction mixture by filtration, and the filtrate was cooled to 0° C., but no phase separation occurred.

While the invention has been described in detail and with reference to specific examples thereof, it will be apparent to one skilled in the art that various changes and modifications can be made therein without departing from the spirit and scope thereof.

What is claimed is:

1. A process for preparing unsaturated dimers of α-methylstyrene, comprising:

dimerizing an α-methylstyrene using an activated clay or an acid clay as a catalyst, in the presence of a carbonic acid ester to form a mixture, and adding said α-methylstyrene incrementally to said mixture in a period of 1 to 10 hours while maintaining the temperature between 50° to 150° C.;

wherein said catalyst is present in an amount of from 0.0005 to 0.1 parts by weight based on the weight of α-methylstyrene, and wherein said carbonic acid ester is a di-$C_{1-4}$ alkyl carbonate or a $C_2$–$C_3$ alkylene carbonate, and is present in an amount of from 0.1 to 1 parts by weight based on the weight of α-methylstyrene.

2. A process as claimed in claim 1, wherein said carbonic acid ester is ethylene carbonate.

3. A process for preparing unsaturated dimers of α-methylstyrene, comprising:

dimerizing α-methylstyrene using activated clay or acid clay as a catalyst and ethylene carbonate as a cocatalyst to form a reaction mixture, separating said reaction mixture into a first phase comprising unreacted α-methylstyrene and a reaction product, and a second phase comprising said catalyst and said ethylene carbonate, and recovering unsaturated dimers of α-methylstyrene from said first phase.

4. A process as claimed in claim 3, further comprising:

separating said catalyst from said second phase by filtration, and recycling said catalyst for said dimerization reaction.

5. A process as claimed in claim 4, further comprising:

cooling said second phase and subjecting said reaction mixture to solid-liquid separation, separating a solid phase comprising ethylene carbonate.

6. A process as claimed in claim 3, further comprising:

isolating said ethylene carbonate from said second phase by liquid-liquid separation, and recycling said ethylene carbonate for said dimerization reaction.

\* \* \* \* \*

UNITED STATES PATENT AND TRADEMARK OFFICE
CERTIFICATE OF CORRECTION

PATENT NO. : 5,481,053
DATED : Jan. 2, 1996
INVENTOR(S) : Masashi INABA, et al.

It is certified that error appears in the above-indentified patent and that said Letters Patent is hereby corrected as shown below:

On the title page, Item [54], the title, should read:

--PROCESS FOR PREPARING ALPHA-METHYLSTYRENE UNSATURATED DIMER--

Signed and Sealed this

Sixteenth Day of April, 1996

Attest:

BRUCE LEHMAN

Attesting Officer

Commissioner of Patents and Trademarks